United States Patent [19]

Enloe et al.

[11] Patent Number: 4,846,825
[45] Date of Patent: Jul. 11, 1989

[54] DIAPERS WITH ELASTICIZED SIDE POCKETS

[75] Inventors: Kenneth M. Enloe; Paul A. Gavronski, both of Neenah; Bonnie L. McMorrow, Appleton, all of Wis.

[73] Assignee: Kimberly-Clark Corporation, Neenah, Wis.

[21] Appl. No.: 115,148

[22] Filed: Oct. 30, 1987

[51] Int. Cl.$^4$ .............................................. A61F 13/16
[52] U.S. Cl. ................................. 604/385.1; 604/385.2
[58] Field of Search ................... 604/385.1, 385.2, 378, 604/389, 397, 398

[56] References Cited

U.S. PATENT DOCUMENTS

| | | | |
|---|---|---|---|
| 3,771,524 | 11/1973 | Ralph | 604/398 |
| 4,597,760 | 7/1986 | Buell | 604/397 |
| 4,695,278 | 9/1987 | Lawson | 604/385.2 |
| 4,704,116 | 11/1987 | Encoe | 604/385.2 |
| 4,747,846 | 5/1988 | Boland et al. | 604/385.1 |

Primary Examiner—Richard J. Apley
Assistant Examiner—J. Welsh
Attorney, Agent, or Firm—John L. Chiatalas

[57] ABSTRACT

According to the instant invention, there is provided an anatomically form-fitting, generally self-adjusting disposable absorbent garment, preferably a diaper. The garment comprises a breathable elastomeric outer cover, resiliently stretchable to surround and closely conform to the contours of a wearer. The outer cover comprises opposed front and rear waistbands, together defining a waist opening, a crotch section disposed between the waistbands, a pair of elasticized leg openings disposed along outer most lateral sides of the crotch section and opposed front and rear panels separated by the crotch section. An absorbent insert structure is defined by opposed front and back waist sections and a pair of side sections connecting the waist sections, including a liquid impermeable backsheet, a bodyside liner essentially coterminous with the backsheet and an absorbent body disposed therebetween. A pair of elasticized flaps, attached to or formed from the bodyside liner, are disposed inwardly of the respective side sections and extend in the crotch section between the front and back waist sections of the insert.

67 Claims, 6 Drawing Sheets

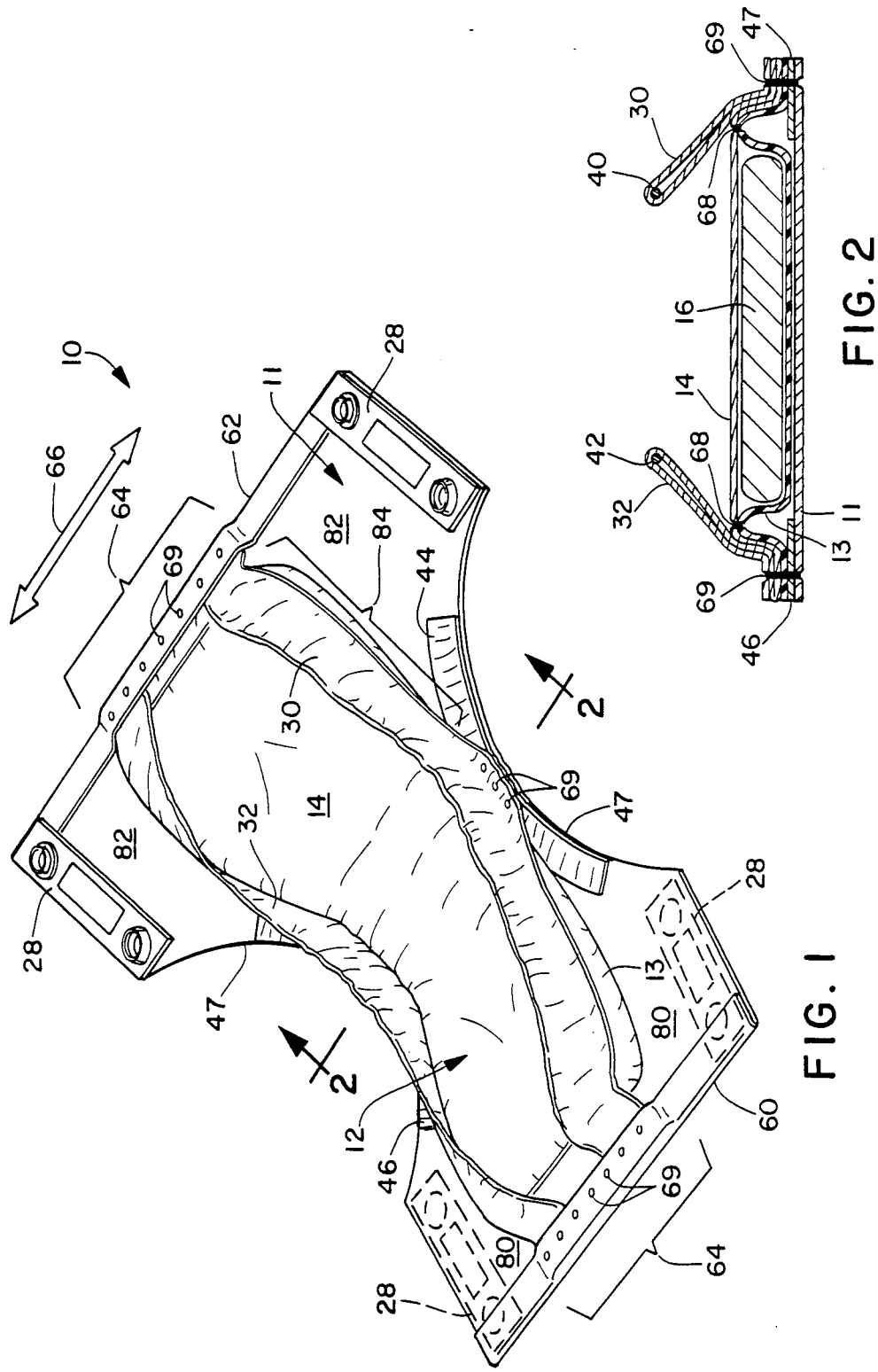

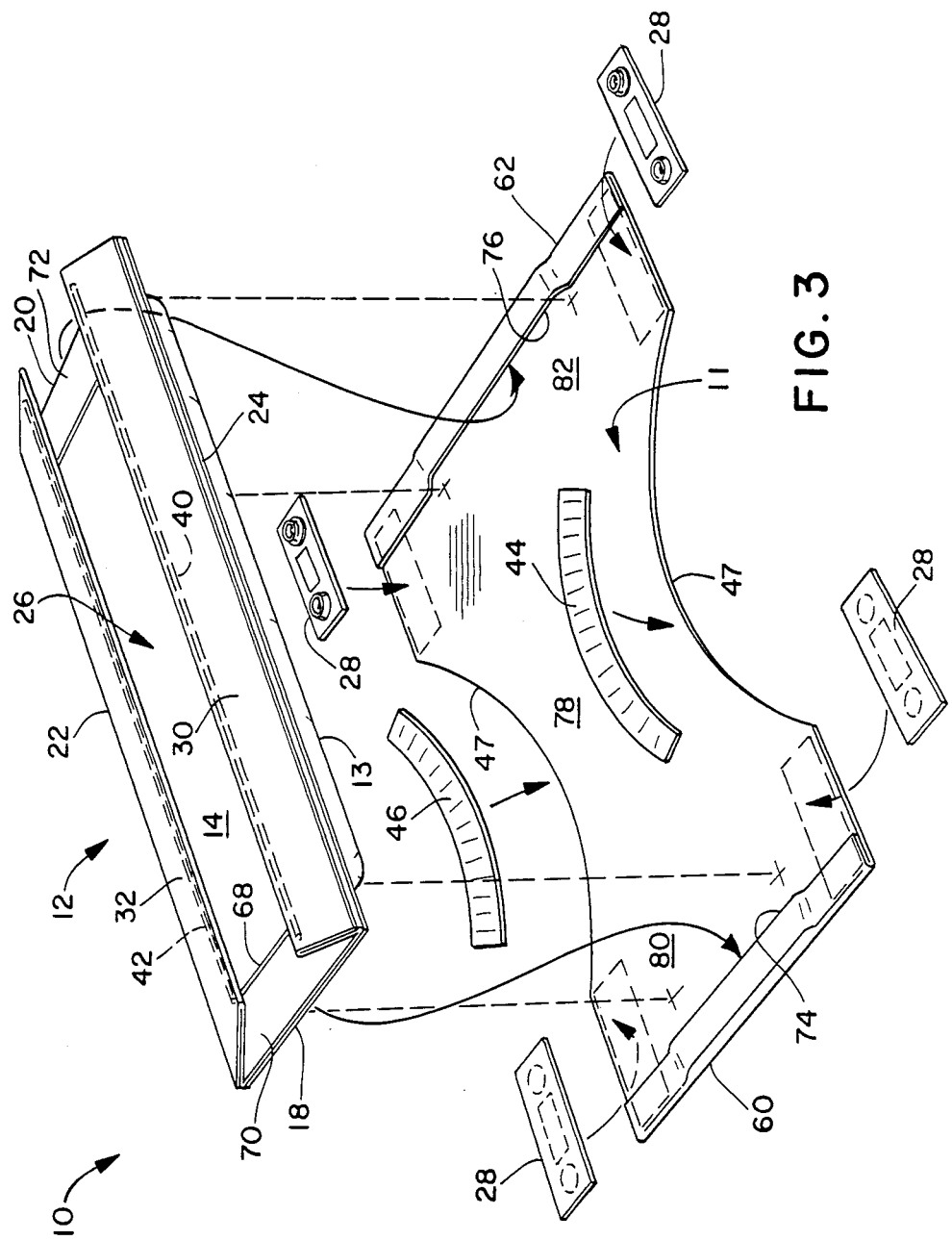

4,846,825

DIAPERS WITH ELASTICIZED SIDE POCKETS

TECHNICAL FIELD

The present invention relates, generally, to the field of disposable garments utilized for the absorption and containment of body exudates. More particularly, the present invention relates to disposable infant and adult diapers with a provision for the sideways containment of fluidic body wastes.

BACKGROUND ART

This invention is an improvement upon the disposable garments of U.S. patent application Ser. No. 786,891 filed Oct. 11, 1985 and now allowed, which is a continuation-in-part of U.S. Ser. No. 67,164 filed July 2, 1984 and now abandoned and European Patent Application No. 214,636, published Mar. 18, 1987, assigned to the instant assignee, the entire disclosures of which are expressly incorporated herein by reference and relied upon. The entire disclosure of U.S. patent application Ser. No. 947,948, filed Dec. 31, 1986 and also assigned to the instant assignee, is also expressly incorporated herein by reference and relied upon.

Disposable garments are generally well known in the art and have become an important and essentially indispensable sanitary protection item, most particularly in the field of infant and child care where disposable diapers provide for the absorption and containment of urine and other body exudates. Present commercially available disposable diapers are generally unitary, preshaped and prefolded, and comprised of a liquid previous bodyside liner, a fluid impervious backing sheet with an absorbent material disposed therebetween. These presently available disposable diapers have met a particular need and have become ever increasingly popular. However, even though the presently available disposable diapers are efficient and effective, they have several drawbacks that have been identified by mothers of infants wearing the diapers. Although the presently available diapers have elasticized leg openings which provide a better fit and enhanced containment of fluid exudates, they have not been entirely successful in stopping leakage from explosive liquified bowel movements and rapid discharges of urine.

Another drawback presently associated with commercially available disposable diapers is skin irritation caused by urine, feces or moisture trapped next to the skin. The feces, if remaining next to the skin, can smear causing problems in cleanup.

The attempts to solve these drawbacks associated with the present commercially available disposable diapers have extended over several years and include the several different concepts discussed below.

A variety of prior diaper constructions have used leg or waist gathers. For example, U.S. Pat. No. 4,324,245 to Mesek, et al. discloses a gathered or bloused design wherein waterproof extruded elastic film is applied to the waist and leg areas of a film barrier backsheet having an absorbent adhered thereto so that the elastic deforms the absorbent structure; again, such an arrangement represents the current state of disposable diapers on the market. Others include U.S. Pat. No. 3,196,872 to Hrubecky showing a rectangular diaper provided with triangular-shaped infolds in the crotch area, U.S. Pat. No. 3,860,003 to Buell wherein the diaper edges are provided with elasticized, flexible flaps along the edge of the absorbent pad in the crotch region and U.S. Pat. No. 4,050,462 to Woon, et al. wherein the diaper is elasticized only along the edges in the narrowed crotch area to create gross transverse rugosities in the crotch area.

U.S. Pat. 3,999,547 to Hernandez discloses a disposable diaper with a waterproof backsheet, a hydrophobic sheet and an absorbent pad sandwiched between the backsheet and the face sheet. The diaper is folded to define a box pleated configuration having a central panel, inwardly extending panels and outwardly extending panels with the inner edges of the inwardly extending panels being in abutting relationship. Sealing strips of waterproof material separate from the backsheet are secured on the face sheet. The sealing strips are formed by folding an excess width of the backsheet over the face sheet forming side flap portions, and then cutting the side flap portions free from the backsheet. The sealing strips may be folded inwardly toward the center of the diaper to form fluid catching seals.

A similar concept is disclosed in U.S. Pat. No. 4,210,143 to De Jonckheere which discloses a disposable diaper for a baby with at least one sheet of flexible liquid impermeable material comprising two longitudinal edges intended to define a waist portion and an absorbent pad superimposed on a central region of the liquid impermeable sheet. The diaper is characterized, in that it comprises, respectively in the immediate vicinity of each of the longitudinal edges, on either side of the pad, flexible longitudinal sheath inside which a flexible longitudinal tie is able to slide and in that each sheath comprises means for gaining access to the corresponding flexible tie in order to enable the latter to be gripped manually and to be tensioned at will in order to reduce the apparent length of the longitudinal edges, to press the latter at will around the baby's legs and to give the disposable diaper the shape of a trough between the legs.

Another concept is shown in U.S. Pat. 4,490,148 to Beckestrom which discloses a protector against incontinence comprising an oblong absorbent body which is fixed to a bottom liquid-tight layer extending outside the absorbent body. The lateral edge portions of the layer are folded in over the absorbent body and form side flaps, the distance between the edges thereof being less than the width of the absorbent body at its mid section. The side flaps are fixed at their ends to the bottom layer. An elastic line, arranged at the edge of each side flap, is designed to contract itself and thereby the edges of the side flaps. When the protector is put on, the edges of the side flaps come into elastic sealing contact in the thigh crease of the crotch.

U.S. Pat. No. 4,040,423 to Jones, discloses longitudinally extending folds or pleats made of fluff which are inflexible, somewhat massive and uncomfortable in that the pleats will not stand and form a smooth curve in conformance with the body when the diaper is worn. Rather, the pleats form corrugations that are bulky to sit upon, that is, the folds or pleats comprise absorbent and do not extend from the liner alone; moreover, when the diaper of Jones is worn, the pleats are unable to shorten their radius of curvature while bent in order to take up the induced slack and maintain the pleat as an effective fluid barrier. U.S. Pat. No. 4,500,316 to Damico is somewhat similar.

However, these attempts to solve one problem have resulted in the emergence of other problems. For example, the elasticized flaps can cause the waterproof material of the flaps to provide a tight seal at the thigh crease because the tensioned elastic presses the easily deformable flaps into close contact with the skin. The waterproof material of the flaps can then cause urine or moisture and even liquid fece material to collect next to the skin and cause skin irritation.

European Patent Application No. 0,219,326 published Apr. 22, 1987 discloses a diaper having dual cuffs wherein a barrier cuff is spaced from the topsheet and a gasketing cuff is formed at the leg opening. Somewhat similarly, U.S. Pat. No. 4,623,342 to Ito discloses pockets formed by means of elasticized leg gathers, particularly at FIGS. 2 and 3 thereof. Neither of these two documents teaches or suggests the use of an elastomeric outer cover. Others have attempted to provide an absorbent structure having elastic placed therein to be more closely conforming to the body of a wearer. For example, Australian Patent Application No. 24850/84, published Sept. 13, 1984, discloses a diaper gathered by an elastic netting panel attached when stretched to the crotch region of the facing sheet. Somewhat similarly, U.S. Pat. No. 4,662,877 to Williams, filed July 30, 1985 and based on Australian Patent Application No. 45217/85, published June 2, 1985, shows a diaper having elastics attached to the crotch portion of the facing sheet inwardly of the leg elastics and either side of a central aperture in the facing sheet. U.S. Pat. No. 4,402,690 to Redfern shows tensioned elastics sewn to the diaper inwardly of the leg openings; however, the leg openings themselves are not elasticized.

Several other draw-backs still remain that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes. Another draw-back identified by these mothers has been the problem associated with skin irritation caused by urine, feces or moisture trapped next to the skin. They have again been very vocal in their desire to obtain disposable diapers that avoid or solve this problem.

In this regard, prior art constructions, such as U.S. Pat. No. 3,658,064 to Pociluyko and U.S. Pat. No. 3,370,590 to Hokanson, et al. have attempted to provide waste containment with a reusable liquid impermeable diaper cover having waterproof pouches or pockets for freely receiving an absorbent, such as a traditional cloth diaper or disposable absorbent; however, the retaining pouches on these supporting garments occlude the skin, covering the target areas at which urine is excreted. U.S. Pat. No. 4,397,646 to Daniels, et al. discloses a reuseable diaper capable of repeated sterilizations in a diaper laundry, comprising elasticized end and side margins and a durable absorbent such as cotton sewn into the crotch area of the waterproof diaper cover, which is a Teflon® coated polyester or equivalent woven material.

U.S. Pat. No. 2,141,105 to Eller discloses a stretchable woven diaperholder for an absorbent pad. U.S. Pat. No. 4,425,128 to Motomura, discloses a diaper cover with sections of waterproof and stretching material in the cover adjacent the fasteners; yet, this construction relies upon reuseable treated woven fabric and many have seam to fully integrate other nonstretchable absorbent components between stretchable diaper ears, effectively eliminating any stretch properties in the front or rear panels or along the waist and leg openings of the diaper cover.

U.S. Pat. Nos. 4,597,761, 4,496,360 and 4,597,670 all disclose multi-component diapering systems comprising an elasticized disposable absorbent insert capable of attachment to a reusable nonstretchable overgarment.

U.S. Pat. Nos. 4,355,425 to Jones, et al., which uses a melt-blown elastic border strip, and 3,644,157 to Draper, both show disposable stretchable panties or shorts rather than diapering garments.

Other approaches have utilized elastic fluid impermeable backing films laminated to an absorbent layer in an attempt to provide enhanced conformability to the body surface, but these films are occlusive to the skin, there is no cooperation of elements elucidated and the integration of the absorbent component restricts the elasticity of the outer cover by the manner in which it is bonded thereto. In this type of construction, the elastic backing film must provide both the barrier function and the fit and conformability functions of the diaper. Such an absorbent dressing is taught by U.S. Pat. No. 4,166,464 to Korpman.

Those references discussed immediately above which have utilized either nonstretchable or stretchable covers functioning both as the diaperholder and liquid barrier have inadequately recognized the problems associated with these approaches, especially the need for functional interactions of the various structural components. Moreover, costly woven diaper covers or overpants, designed to be reusable, do not offer true disposability.

In summary, there still exists a need for an improved disposable garment which contains and absorbs the sideways flow of urine and other fluid body wastes. There is a still further need for an anatomically form-fitting, generally self-adjusting disposable absorbent garment providing such enhanced sideways containment and absorption of fluid waste.

SUMMARY OF THE INVENTION AND ADVANTAGES

According to the instant invention, there is provided an anatomically form-fitting, generally self-adjusting disposable absorbent garment comprising a breathable elastomeric outer cover, comprising opposed front and rear waistbands defining a waist opening, a crotch section disposed between the waistbands, a pair of elastically contractable leg openings delimited along opposed marginal side edges of the crotch section and opposed front and rear panels separated by the crotch section. An absorbent insert structure is substantially superposable on the outer cover and includes a liquid impervious backsheet, a liquid pervious bodyside liner essentially coterminous with the backsheet and an absorbent body disposed therebetween. The insert defines a shape having opposed front and back waist sections and first and second opposed connecting side sections connecting the waist sections. A pair of elastically contractable fluid pervious flaps comprise fixed edges attached to or formed from the bodyside liner and free edges, disposed inwardly of the connecting sides, the flaps extending at least in the crotch section between the front and back waist sections of the insert and the free edges of the flaps are each spaced from the surface of the liner when the garment is worn.

In one preferred embodiment, the outer cover comprises an elastomeric nonwoven fabric, preferably a stretch-bonded laminate formed from an elastic nonwoven web joined to one or more gatherable nonwoven webs.

In another preferred embodiment, the outer cover is resiliently stretchable from 20 to 200%, preferably in an essentially cross-body direction.

In another preferred embodiment, the flaps are essentially rectangular in shape with first and second longitudinal sides extending essentially parallel with respect to a line centered on the longitudinal axis of the garment wherein the center line lies equidistantly between the respective side sections, the longitudinal sides being connected by base sides and both the longitudinal sides and the base sides having preselected dimensions.

In another preferred embodiment, the longitudinal sides of the flaps have a length sufficient to extend from the front waist section to the back waist section and a width sufficient for a longitudinal side of each flap to be essentially coterminous with the center line of the garment.

In another preferred embodiment, each of the flaps has at least one elastic member applied to the flap with a tension sufficient to cause the flap to conform to the wearer's shape; further, an additional elastic member may be applied intermediate the first elastic member and the other longitudinal side of the flap, the second elastic member being applied with a tension different than that of the first elastic member wherein the two elastic members cooperate to cause the flaps to conform to the shape of the wearer.

In another preferred embodiment, the flaps may be attached to or formed from the bodyside liner along a pair of curved lines disposed symmetrically on each side of the center line of the garment and the curved attachment lines may either diverge from or alternatively converge toward the center line of the garment.

An advantage of the present invention is a disposable absorbent garment, such as a diaper, having an absorbent structure with waste containment flaps or pockets along the leg openings thereof, enhancing the sideways containment and absorption of urine and other fluid body exudates, such as liquified fecal material.

Another advantage of the present invention is an anatomically form-fitting, generally self-adjusting disposable absorbent garment which is aesthetically pleasing.

A further advantage of the present invention is consistent, proper positioning of the absorbent structure relative to the body by means of a breathable elastomeric outer cover, the cover and the absorbent structure cooperating together to achieve enhanced containment and absorption of body wastes.

Other objects of the present invention in terms of both construction and mode of operation, as well as full appreciation for its manufacture and use, will be gained from an examination of the following detailed description of the modes for carrying out the invention, read in conjunction with the figures of the drawing.

BRIEF DESCRIPTION OF THE DRAWINGS

The present invention will be more fully understood and further advantages will become apparent when reference is made to the following detailed description of the invention and the drawings, in which:

FIG. 1 is an internal perspective view of the garment of the present invention;

FIG. 2 is a sectional view taken along lines 2—2 of FIG. 1;

FIG. 3 is an exploded perspective view of the garment of the present invention;

MODES FOR CARRYING OUT THE INVENTION

Figure 4:
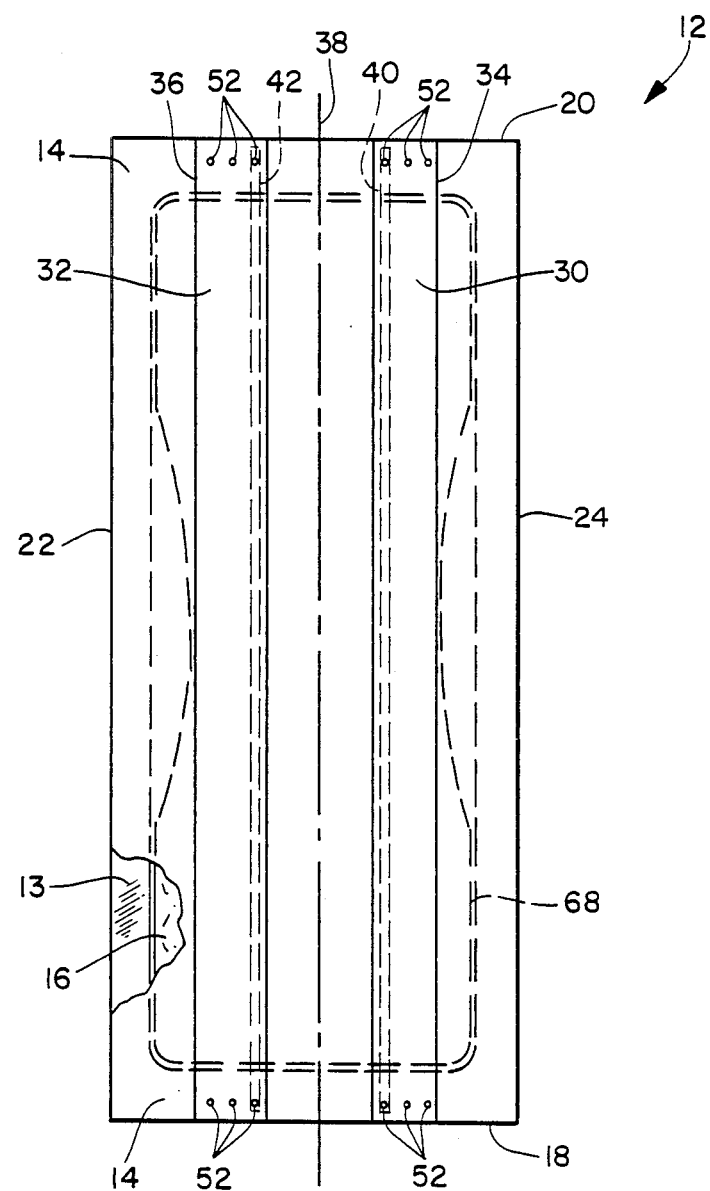
FIG. 4 is a plan view of an absorbent insert structure of the present invention showing full-length flaps with an elastic member in each flap.

The present invention relates, generally, to disposable garments utilized for the absorption and containment of urine and other body exudates. The present invention relates more specially to disposable garments that are utilized for the absorption and containment of liquids and fluidic body exudates such as fluidic fecal material. Most particularly, the present invention provides at least one pair of flaps, which may be elasticized, to slow the sideways flow of liquids, such as urine, and to essentially prevent the sideways flow of fluidic solids, such as fluidic fecal material. Accordingly, the present invention will now be described with reference to certain modes for carrying out the invention within the aforementioned context. Those skilled in the art will realize that such a description is meant to be exemplary only and should not be deemed limitative respecting the scope of the present invention, for example, in terms of its construction.

Referring to FIG. 1, the disposable diaper 10 comprises a nonwoven elastomeric outer cover 11 having an absorbent insert structure 12 integrated thereinto as will be described below. The insert 12 comprises a liquid impervious backsheet 13, a liquid pervious bodyside liner 14 and an absorbent body 16 disposed between backsheet 13 and bodyside liner 14. The bodyside liner 14 is made from a liquid pervious material such as a carded or spunbonded web of polymeric fibers and backsheet 13 is made from a liquid impervious material such as an extruded polymeric film.

Referring to FIG. 3, the bodyside liner 14 and backsheet 13 are essentially coterminous and form a shape with a front waist section 18, a back waist section 20 and two connecting side sections, indicated by numerals 22, 24, connecting the waist sections 18, 20. Intermediate the front waist section 18 and back waist section 20 is a crotch section, indicated by numeral 26. The garment is typically placed around a wearer, such as an infant, and held in place with fastening means, such as the cooperating fastener members each shown at 28. Other fastening means can be used without departing from the scope of the present invention, as will be discussed herein.

Referring to FIGS. 4–7, the instant absorbent insert 12 includes a pair of flaps 30, 32 each having fixed edges which are attached to or formed from bodyside liner 14 along lines 34, 36, respectively. In either case, the crease formed along lines 34, 36 may be "sealed" i.e., by a continuous sonic bond or by a strip of adhesive. The sealing of the crease increases the ability of the absorbent structure to maintain its shape and increases the resistance to leakage therefrom. Alternatively, the crease can consist of a series of spotbonds. The flaps 30, 32 are attached to, or formed from bodyside liner 14, inwardly of the sides 24, 22, respectively, of the insert 12. As can be appreciated, if flaps 30, 32 are formed from bodyside liner 14, the flaps are the same material as bodyside liner 14. However, if the flaps are attached to bodyside liner 14, the flaps 30, 32 may be made from a different material. The preferred material for flaps 30, 32 is a liquid pervious nonwoven material. The flaps 30, 32 may be folded inwardly (FIG. 3) toward a center line 38 and bonded at each end to the bodyside liner 14. Flaps 30, 32 form pockets into which solid fecal material collects and is contained. Alternately, fluidic fecal material is collected by the pockets and is essentially strained allowing the liquid portion to be absorbed by the absorbent pad or body of the garment. Flaps 30, 32 may have at least one elastic member, indicated at 40, 42 applied thereto along a free edge of each flap whereby the elasticized free edges of the flaps are spaced from the surface of the liner. As indicated in FIGS. 1 and 2, the elastic members 40, 42 may be applied essentially at the inwardly directed edge of flaps 30, 32. Also indicated in FIGS. 1 and 3, the disposable diaper 10 may additionally have elastic members 44, 46 attached along the leg openings 47 of the outer cover 11 to gather the leg openings about the legs of the wearer. A method of imparting elasticity to the leg gathers is by bonding, e.g., ultrasonically, the gathers 44, 46 along the leg openings while the gathers are in a stretched condition.

Figure 5:
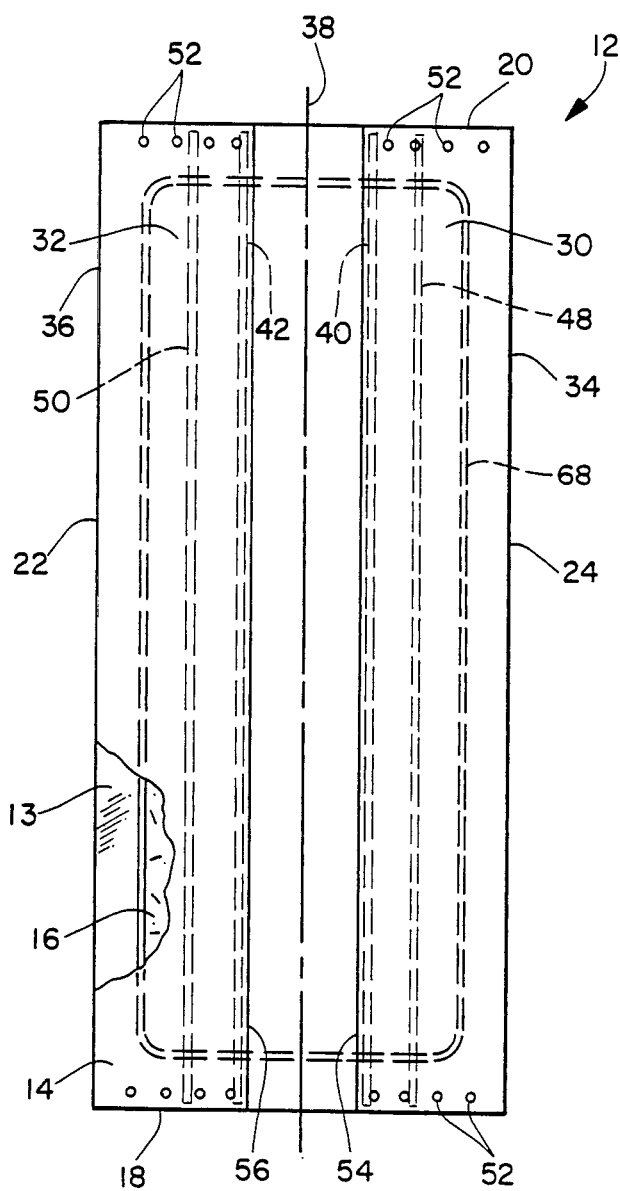
FIG. 5 is a plan view of an absorbent insert structure of the present invention showing full-length flaps with two elastic members in each flap.

In the alternative embodiment referred to in FIGS. 4 or 5, flaps 30, 32 have a width sufficient so that inwardly directed edges of the flaps are essentially coterminous with center line 38. In addition, flaps 30, 32 may have at least a second elastic member 48, 50 disposed in respective flaps. The second elastic member is applied to the flap intermediate to the first elastic member and the lines 34, 36 respectively. The first elastic member in each flap is applied with a first preselected tension sufficient to cause each flap to conform to the shape of a wearer. The second elastic member in each flap, if applied, is applied with a second preselected tension which may be greater than, less than or equal to the first preselected tension. However, the tensions are selected to cooperate so that the flaps conform to the shape of a wearer. The width of the flaps can be formed about one-half inch to a width sufficient for the inwardly directed edge of each flap to be essentially coterminous with the centerline 38 as shown in FIGS. 3 and 4.

Flaps 30, 32 with elastic members 40, 42, respectively, applied to the flaps 30, 32 are shown in FIG. 4. Indicated at 52 are bonds bonding respective ends of flaps 30, 32 to bodyside liner 14 at the front waist section 18 and back waist section 20. Any method of bonding may be used. A preferable method of bonding is autogenous bonding such as sonic bonding. Another method that is acceptable is adhesive bonding.

FIG. 5 shows flaps 30, 32 having more width and having at least second elastic members 48, 50 applied to flaps 30, 32, respectively. The second elastic members are applied intermediate to lines 34, 36 and inwardly directed edges 54, 56 of flaps 30, 32. Again it should be noted that the width of flaps 30, 32 can vary and the illustrations and descriptions herein are for illustrative purposes only.

Figure 6:
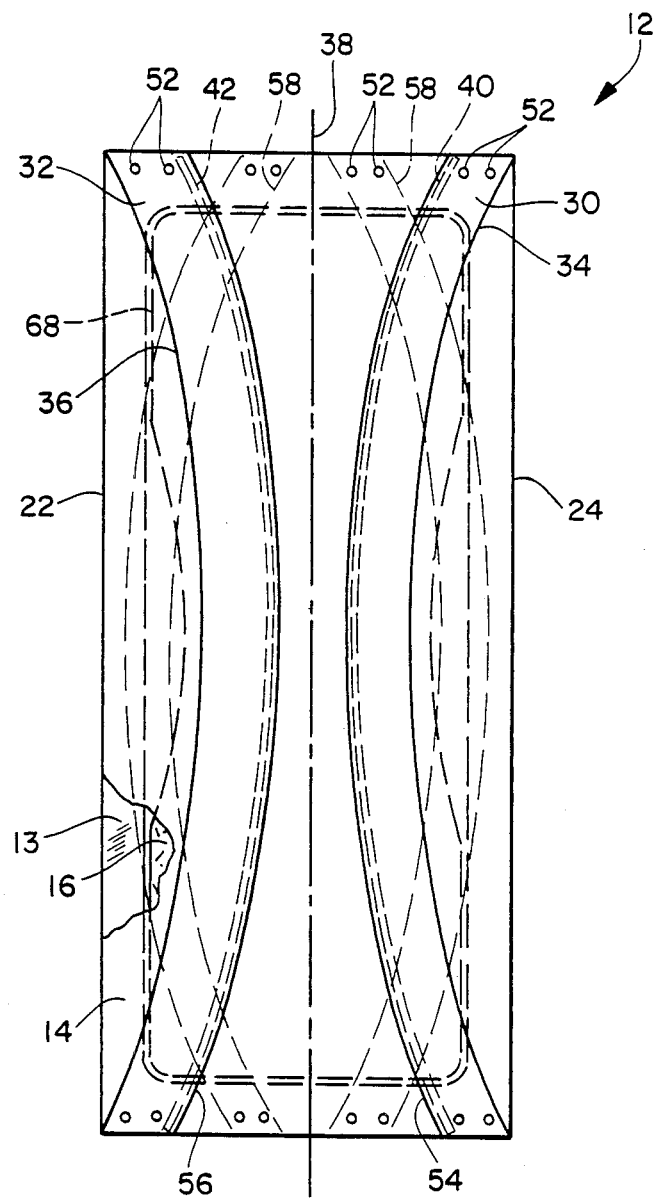
FIG. 6 is a plan view of an absorbent insert structure of the present invention showing full-length curved flaps.

Illustrated in FIG. 6 are flaps 30, 32 which are formed from or attached to inner liner 14 along lines 34, 36, respectively, wherein lines 34, 36 are curved in relation to centerline 38. The lines 34, 36 may either diverge from centerline 38 or the lines 34, 36 may converge toward the centerline 38, as shown by phantom line 58. As before, flaps 30, 32 may be folded and bonded to inner liner 14 at respective ends of each flap. The flaps are folded and bonded whereby edges 54, 56 are directed toward centerline 38.

Figure 7:
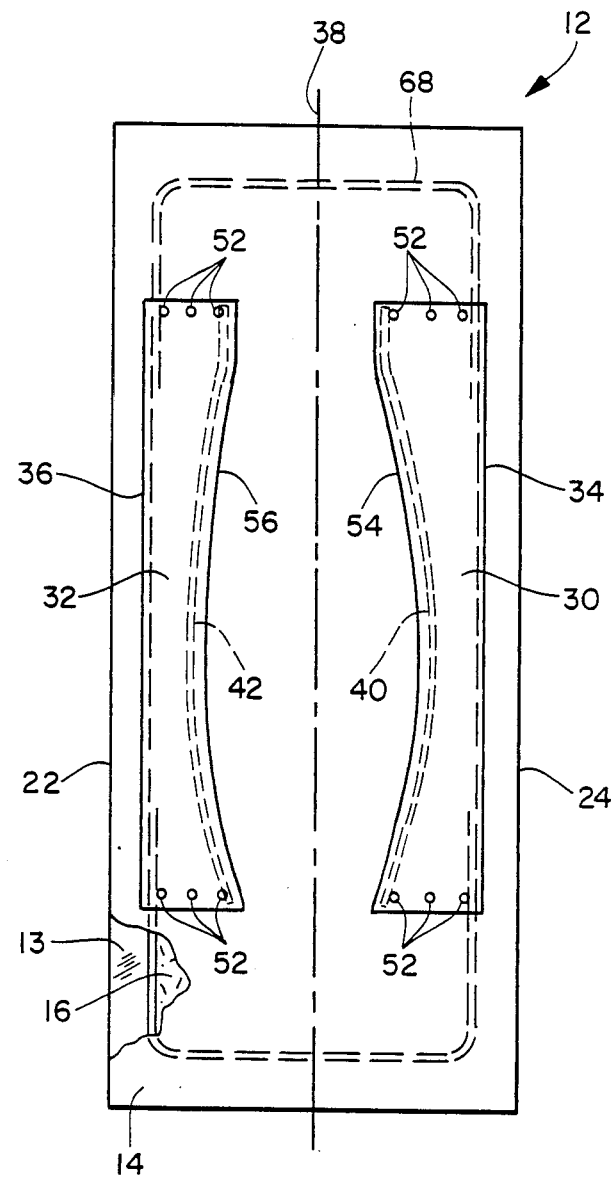
FIG. 7 is a plan view of an absorbent insert structure of the present invention showing partial flaps of varying width.

The alternative embodiment of the invention shown in FIG. 7 comprises flaps 30, 32 with varying width and with a length that extends from a first portion of the garment to a second portion of the garment where the total extent of the flaps is less than the full length of the garment. Typically, the flaps extend at least through the crotch section of the garment. Illustrated in FIG. 7 are flaps 30, 32, which have a width wider at respective ends of the flaps 30, 32 than at an intermediate portion of the flaps; however, it is comprehended within the scope of this invention that flaps 30, 32 may have a width wider at an intermediate portion of flaps than at respective ends. Also comprehended are combinations of concepts described above wherein varying width flaps are attached to or formed from inner liner 14 along curved lines which converge to or diverge from centerline 38.

The elastomeric outer cover 11 has the absorbent insert 12 attached and integrated thereinto in the manner taught by the above-referenced United States Patent Application Ser. No. 947,948 wherein the outer cover comprises a breathable nonwoven elastomeric fiber. The fabric is preferably a stretch-bonded laminate wherein an elastic nonwoven web is joined to one or more gatherable nonwoven webs. The outer cover 11 structurally and functionally cooperates with the absorbent insert 12, attachment means being provided for attaching and integrating the insert into the outer cover while allowing substantially unrestricted functional stretchability thereof. The attachment means allow the insert 12, which is typically of nonstretchable materials, to cooperate functionally with the elastomeric outer cover 11 while still allowing the cover 11 to perform the separate function of positioning the insert properly on the wearer's body and providing an aesthetically pleasing appearance. The insert 12 performs the separate function of absorbing and containing body wastes while properly positioned on the body by the outer cover 11. The absorbent insert has longitudinal opposed waist sections 18, 20 which are respectively attached adjacent the front 60 and rear 62 waistband portions of the outer cover 11 in selected waist attachment zones 64. The outer cover is preferably resiliently stretchable in an essentially cross-body direction (arrow) 66 transverse to the centerline 38 from about 20% to about 200% and, as stated above, separately functions to position the absorbent insert in registration with the body, while the absorbent insert contains and absorbs the body exudates. Accordingly, the elastomeric outer cover 11 need not perform a liquid barrier function; rather, this function is effectively performed by the liquid impermeable backsheet 13 of the absorbent insert 12.

Leakage of wastes from the absorbent insert 12, particularly urine, is avoided by forming a continuous seal, preferably at ultrasonic bond 68, between the liner 14 and backsheet 13 about the perimeter of the absorbent core 16.

The waist sections 18, 20 of the insert 12 may form attachment flaps 70, 72, respectively, and be attached by bonds 69, e.g., ultrasonically, within hems 74, 76 at the waist portions 60, 62 of the outer cover 11, as shown in FIGS. 1 and 3.

It has been found that the combination of a resiliently stretchable outer cover and an absorbent insert having the leg flaps 30, 32 constructed in accordance with the above-described embodiments of the present invention results not only in an improved fit and appearance, but also in an enhanced containment of fluidic body wastes, particularly semi-solid fecal material, so that sideways leakage of wastes at the legs of the wearer is reduced.

Although the leg openings 47 of the elastomeric outer cover 11 are also elasticized, supplemental elastication thereof may be provided by gathers 44, 46 mentioned above. For this purpose, the material disclosed in the above-referenced U.S. Application Ser. No. 947,948 is preferred, wherein a nonself-adhering elastomeric film is sandwiched and ultrasonically bonded between a pair of gatherable nonwoven facing sheets, thereby creating breathable apertures in the elastic laminate. Although not necessary, the side sections 22, 24 may be bonded at points 69 in the central portion of the leg openings 47 to further lessen any sideways shifting of the insert, which may occur in the crotch section 78.

The outer cover of the present invention may be ultrasonically bonded to the absorbent insert 12 while the outer cover is in a stretched condition; however, by properly limiting the bonded points between the insert and cover, as taught herein, the outer cover need not be prestretched and bonded to the insert. Specifically, the waist attachment zones 64 may be minimal in length and the attachment flaps 70, 72 (FIG. 3) may be narrowed to reduce the length between bond points at the outermost lateral ends of the waist attachment zones 64.

The term stretchability as used herein is defined by the following relationship:

$$\text{stretchability} = ((\text{final dimension} - \text{initial dimension})/\text{initial dimension}) \times 100\%$$

Since the outer cover 11 is also resilient, the outer cover returns essentially to its initial dimension when the stretching force is removed. Suitable resiliently stretchable materials are disclosed in U.S. Pat. Nos. 4,663,220 and 4,657,802 and Application Ser. No. 760,437 of the instant assignee, the entire disclosures of which are hereby incorporated by reference and relied upon.

The outer cover 11 comprises front 80 and rear 82 panels which are separated by the crotch portion 78. The insert is substantially superposed on the panels 80, 82 and crotch section so that one or more free-span zones 84 are defined in the outer cover underlying the insert 12 wherein there is an absence of attachment of the insert 12 to the outer cover 11. Such a free-span zone 84 in the outer cover 11 is shown underlying the insert 12 in the rear panel 82 where cross-body stretchability has been found to be most important for proper fit and appearance of the garment when worn. As stated above, the side sections 22, 24 of the insert 12 need not be attached along or at the leg openings 47 of the outer cover 11, instead the insert need only be attached at the attachment flaps 70, 72 to prevent downward sagging of the insert when wet during wear. Thus, in this case, a single free-span zone 84 would be defined underlying the insert 12 in the area between the front 60 and rear 62 waistbands of the outer cover 11.

It is to be clearly understood the description of methods for making materials suitable for the outer cover and the description of materials for use as the outer cover is exemplary only and is not meant to be limiting. Other resiliently stretchable materials could be used without departing from the spirit and scope of the present invention.

Thus, while the invention has now been described with reference to several preferred embodiments and illustrated with regard to a range of optional features, those skilled in the art will appreciate that various substitutions, omissions, modifications and changes may be made without departing from the spirit hereof. Accordingly, it is intended that the foregoing description be deemed merely exemplary of the preferred scope of the present invention and not to be deemed a limitation thereof.

We claim:

1. An anatomically form-fitting, generally self-adjusting disposable absorbent garment comprising:
   a breathable elastomeric outer cover including front and rear waistband portions defining a waist opening, a crotch section disposed between said waistbands, a pair of elastically contractable leg openings delimited along opposed marginal side edges of said crotch section and opposed front and rear panels separated by said crotch section;
   an absorbent insert structure substantially superposable on said front and rear panels and said crotch section, including a liquid pervious bodyside liner and a liquid impervious backsheet with an absorbent core disposed therebetween, defining a shape having a front waist section and a back waist section with first and second opposed connecting sides connecting said waist section, said connecting sides being equidistantly spaced with respect to a line centered on the longitudinal axis of said garment;
   attachment means for attaching and integrating said insert to said outer cover while allowing substantially unrestricted functional stretchability thereof; and
   first and second elastically contractable, fluid pervious flaps, attached to or formed from said liner and disposed inwardly of said connecting sides, respectively, defining a pair of elasticized waste-containment pockets along each of said connecting sides of said absorbent structure.

2. The garment of claim 1, wherein each of said first and second fluid pervious flaps comprises an essentially rectangular shape with first and second longitudinal sides and first and second base sides 3. The garment of claim 2, wherein each of said first and second flaps is attached to or formed from said bodyside liner along respective first and second lines wherein said first and second lines are essentially parallel to said centerline of said garment.

4. The garment of claim 3, wherein each of said first and second longitudinal sides have a preselected length and each of said first and second base sides have a preselected width.

5. The garment of claim 4, wherein a first longitudinal side of each of said flaps is attached to or formed from said bodyside liner along respective ones of said first and second lines.

6. The garment of claim 5, wherein said first longitudinal side of each of said flaps has a length sufficient to extend from said front waist section to said back waist section along said respective first and second lines.

7. The garment of claim 6, wherein said first longitudinal side of each of said flaps is sealed to said bodyside liner along said respective first and second lines.

8. The garment of claim 7, wherein said first and second base sides are attached to or formed from said bodyside liner wherein a second longitudinal side of each of said flaps is directed toward said centerline of said garment.

9. The garment of claim 8, wherein each of said elasticized flaps is elasticized by at least one elastic member applied thereto.

10. The garment of claim 9, wherein said at least one elastic member is applied to each of said flaps with a first preselected tension.

11. The garment of claim 10, wherein said first preselected tension is sufficient to cause said second longitudinal side of each of said flaps to conform to a shape of a wearer.

12. The garment of claim 11, wherein each of said flaps has at least a second elastic member applied thereto.

13. The garment of claim 12, wherein said at least a second elastic member is applied intermediate said at least one elastic member and said first longitudinal side and wherein said at least a second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

14. The garment of claim 13, wherein said preselected width of said first and second base sides is selected to be in the range of about one half inch to a width sufficient for said second longitudinal side to be essentially coterminous with said centerline.

15. The garment of claim 2, wherein each of said first and second flaps is attached to or formed from said bodyside liner along respective first and second lines wherein said first and second lines are curved and symmetrically oppositely disposed on each side of said centerline of said garment.

16. The garment of claim 15, wherein said first and second lines are mutually divergent from said centerline in at least one of said front waist section or said back waist section.

17. The garment of claim 16, wherein said first and second lines are mutually divergent from said centerline in said front waist section.

18. The garment of claim 17, wherein each of said first and second longitudinal sides has a preselected length and said first and second base sides have a preselected width.

19. The garment of claim 18, wherein a first longitudinal side of each of said flaps is attached to or formed from said bodyside liner along respective ones of said first and second lines.

20. The garment of claim 19, wherein said first longitudinal side of each of said flaps has a length sufficient to extend from said front waist section to said back waist section along said first and second curved lines.

21. The garment of claim 20, wherein said first and second base sides are attached to or formed from said bodyside liner wherein a second longitudinal side of each of said flaps is directed toward said centerline of said garment.

22. The garment of claim 21, wherein each of said flaps has at least one elastic member applied thereto.

23. The garment of claim 22, wherein said at least one elastic members is applied essentially at said second longitudinal side.

24. The garment of claim 23, wherein said at least one elastic member is applied to each of said flaps with a first preselected tension.

25. The garment of claim 24, wherein said first preselected tension is sufficient to cause said second longitudinal side of each of said flaps to conform to a shape of a wearer.

26. The garment of claim 25, wherein each of said flaps has at least a second elastic member applied thereto.

27. The garment of claim 26, wherein said second elastic member is applied intermediate said one elastic member and said first longitudinal side and wherein said second elastic members is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

28. The garment of claim 27, wherein said preselected width of said first and second base sides of each of said flaps is selected to be in the range of about one half inch to a width sufficient for each of said second longitudinal sides of each of said flaps to be essentially coterminous with said centerline.

29. The garment of claim 5, wherein said first longitudinal side of each of said flaps has a length sufficient to extend from a first portion of said absorbent structure to a second portion of said absorbent structure.

30. The garment of claim 29, wherein said first longitudinal side of each of said flaps has a length sufficient to extend from a first portion of said absorbent structure to a second portion of said absorbent structure along respective said first and second lines which extend through said crotch section of said absorbent structure wherein said crotch section is intermediate said front waist section an said back waist section.

31. The garment of claim 30, wherein said first and second base sides of each of said flaps are attached to or formed from said bodyside liner whereby a second longitudinal side of each of said flaps is directed toward said centerline of said garment.

32. The garment of claim 31, wherein each of said flaps has at least on elastic member applied thereto.

33. The garment of claim 32, wherein said one elastic member of each of said flaps is applied essentially at said second longitudinal side.

34. The garment of claim 33, wherein said one elastic member is applied to each of said flaps with a first preselected tension.

35. The garment of claim 34, wherein said first preselected tension is sufficient to cause said second longitudinal side of each of said flaps to conform to a shape of a wearer.

36. The garment of claim 35, wherein each of said flaps has at least a second elastic member applied thereto.

37. The garment of claim 36, wherein said second elastic member is applied intermediate said one elastic member of each of said flaps and said first longitudinal side and wherein said at least a second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

38. The garment of claim 37, wherein said preselected width of said first and second base sides is selected to be in the range of about one half inch to a width sufficient for said second longitudinal side to be essentially coterminous with said centerline.

39. The garment of claim 18, wherein said first longitudinal side of each of said flaps has a length sufficient to extend from a first portion of said absorbent structure to a second portion of said absorbent structure.

40. The garment of claim 39, wherein said first longitudinal side of each of said flaps has a length sufficient to extend from a first portion of said absorbent structure to a second portion of said absorbent structure along respective ones of said first and second curved lines which extend through said crotch section of said absorbent structure.

41. The garment of claim 40, wherein said first and second base sides of each of said flaps are attached to said bodyside liner whereby a second longitudinal side of each of said flaps is directed toward said centerline of said garment.

42. The garment of claim 41, wherein each of said flaps has at least one elastic member applied thereto.

43. The garment of claim 42, wherein said one elastic member of said flaps is applied essentially at said second longitudinal side.

44. The garment of claim 43, wherein said one elastic member is applied to each of said flaps with a first preselected tension.

45. The garment of claim 44, wherein said first preselected tension is sufficient to cause said second longitudinal side of each of said flaps to conform to a shape of a wearer.

46. The garment of claim 45, wherein each of said flaps has at least a second elastic member applied thereto.

47. The garment of claim 46, wherein said second elastic member is applied intermediate said one elastic member and said first longitudinal side of each of said flaps and wherein said second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

48. The garment of claim 47, wherein said preselected width of said first and second base sides of each of said flaps is selected to be in the range of about one half inch to a width sufficient for each of said second longitudinal sides of each of said flaps to be essentially coterminous with said centerline of said garment.

49. An anatomically form-fitting, generally self-adjusting disposable absorbent garment comprising:
a breathable elastomeric outer cover including front and rear waistband portions defining a waist opening, a pair of elastically contractable leg openings delimited along marginal side edges of said outer cover, a crotch section disposed between said leg openings and front and rear panels separated by said crotch section;
an absorbent insert structure substantially superposable on said front and rear panels and said crotch section, including a liquid pervious bodyside liner and a liquid impervious backsheet with an absorbent body disposed therebetween, defining a shape having a front waist section and a back waist section with first and second opposed connecting sides connecting said waist sections, said connecting sides being equidistantly spaced with respect to a line centered on the longitudinal axis of said garment;
attachment means for attaching and integrating said insert to said outer cover while allowing substantially unrestricted functional stretchability thereof; and
first and second elasticized fluid pervious flaps each having a longitudinal side, a first and second base side and a fourth side wherein a distance between said longitudinal side and said fourth side comprises a width of said flaps and wherein said width varies between said first and second base side and wherein said longitudinal side is attached or formed from said bodyside liner and spaced inwardly of said elasticized leg openings, respectively, defining a pair of elasticized waste containment pockets.

50. The garment of claim 49, wherein each of said first and second flaps is attached to or formed from said bodyside liner along respective first and second lines which are symmetrically disposed on opposed first and second sides of said centerline.

51. The garment of claim 50, wherein said flaps have a preselected length.

52. The garment of claim 51, wherein said preselected length is sufficient to extend from a first portion of said absorbent structure to a second portion of said absorbent structure.

53. The garment of claim 52, wherein said preselected length is sufficient to extend from said front waist section to said back waist section of said absorbent structure along said first and second lines.

54. The garment of claim 53, wherein each of said flaps has at least one elastic member applied thereto.

55. The garment of claim 54, wherein said one elastic member is applied essentially at said fourth side of each of said flaps.

56. The garment of claim 55, wherein said one elastic member is applied to each of said flaps with a first preselected tension.

57. The garment of claim 56, wherein said first preselected tension is sufficient to cause said fourth side of each of said flaps to conform to a shape of a wearer.

58. The garment of claim 57, wherein each of said flaps has at least a second elastic member applied thereto.

59. The garment of claim 58, wherein said second elastic member is applied intermediate said at least one elastic member and said longitudinal side of each of said flaps and wherein said second elastic member is applied with a second preselected tension wherein said second preselected tension can be greater than, less than or equal to said first preselected tension and wherein said first and second preselected tensions are selected to cooperate to cause said fourth side of each of said flaps to conform to a shape of a wearer.

60. An anatomically form-fitting, generally self-adjusting disposable absorbent garment comprising:
a breathable elastomeric outer cover including front and rear waistband portions defining a waist opening, a pair of elastically contractable leg openings delimited along marginal side edges of said outer cover, a crotch section disposed between said leg openings and front and rear panels separated by said crotch section;

an absorbent insert structure substantially superposable on said front and rear panels and said crotch section, including a liquid pervious bodyside liner and a liquid impervious backsheet with an absorbent body disposed therebetween, defining a shape having a front waist section and a back waist section with first and second opposed connecting sides connecting said waist sections, said connecting sides being equidistantly spaced with respect to a line centered on the longitudinal axis of said garment;

attachment means for attaching and integrating said insert to said outer cover while allowing substantially unrestricted functional stretchability thereof; and first and second elasticized liquid pervious flaps, formed from said bodyside liner and spaced inwardly of said first and second connecting sides, respectively, defining a pair of elasticized waste containment pockets.

61. The garment of claim 60, wherein each of said first and second flaps is formed along respective first and second opposed lines which are symmetrically disposed with respect to said centerline of said garment.

62. The garment of claim 61, wherein each of said flaps extends from said front waist section to said back waist section of said absorbent structure along said first and second lines.

63. The garment of claim 62, wherein each end of said flaps is attached to said bodyside liner whereby said flaps are directed toward said centerline of said garment.

64. The garment of claim 63, wherein each of said elasticized flaps is elasticized by at least one elastic member applied thereto.

65. The garment of claim 64, wherein said one elastic member of each of said flaps is applied with a preselected tension sufficient to cause said flap to conform to the shape of a wearer.

66. The garment of claim 65, wherein each of said flaps has at least a second elastic member applied thereto.

67. The garment of claim 66, wherein said second elastic member of each of said flaps is applied with a tension selected to cooperate with said preselected tension of said one elastic member of each of said flaps to cause each of said flaps to conform to a shape of a wearer of said garment.

* * * * *